United States Patent
Darley

(10) Patent No.: US 7,856,986 B2
(45) Date of Patent: Dec. 28, 2010

(54) MAGNETIC ALIGNMENT APPARATUS FOR A TRANSCUTANEOUS TRANSFER SYSTEM

(75) Inventor: Derek Ian Darley, Cromer Heights (AU)

(73) Assignee: Cochlear Limited, Lane Cove (AU)

( * ) Notice: Subject to any disclaimer, the term of this patent is extended or adjusted under 35 U.S.C. 154(b) by 884 days.

(21) Appl. No.: 10/866,034

(22) Filed: Jun. 14, 2004

(65) Prior Publication Data

US 2004/0260362 A1  Dec. 23, 2004

(30) Foreign Application Priority Data

Jun. 13, 2003  (AU) .............................. 2003902964

(51) Int. Cl.
*A61B 19/00* (2006.01)
(52) U.S. Cl. ..................................... 128/899
(58) Field of Classification Search ................. 128/899, 128/897; 600/25–28; 607/57, 61, 115; 623/10
See application file for complete search history.

(56) References Cited

U.S. PATENT DOCUMENTS

| 4,726,378 | A | | 2/1988 | Kaplan |
| 4,736,747 | A | | 4/1988 | Drake |
| 5,603,726 | A | * | 2/1997 | Schulman et al. ............. 607/57 |
| 6,308,101 | B1 | * | 10/2001 | Faltys et al. ................... 607/57 |
| 6,668,065 | B2 | * | 12/2003 | Lee et al. ..................... 381/380 |

* cited by examiner

*Primary Examiner*—Charles A Marmor, II
*Assistant Examiner*—Christine D Hopkins
(74) *Attorney, Agent, or Firm*—Kilpatrick Stockton LLP

(57) ABSTRACT

In one embodiment of the invention, a transcutaneous transfer system is disclosed. The system comprises: an inductively-coupled coil system comprising an external and an internal coil adapted to be transcutaneously juxtaposed along a coupling axis; an internal magnet fixed relative to the internal coil; an external magnet assembly coupled to the external coil; and an apparatus to securely retain the magnet assembly in a desired one of a plurality of positions along a longitudinal axis substantially parallel to the coupling axis in response to tool-less manipulation of the apparatus.

27 Claims, 6 Drawing Sheets

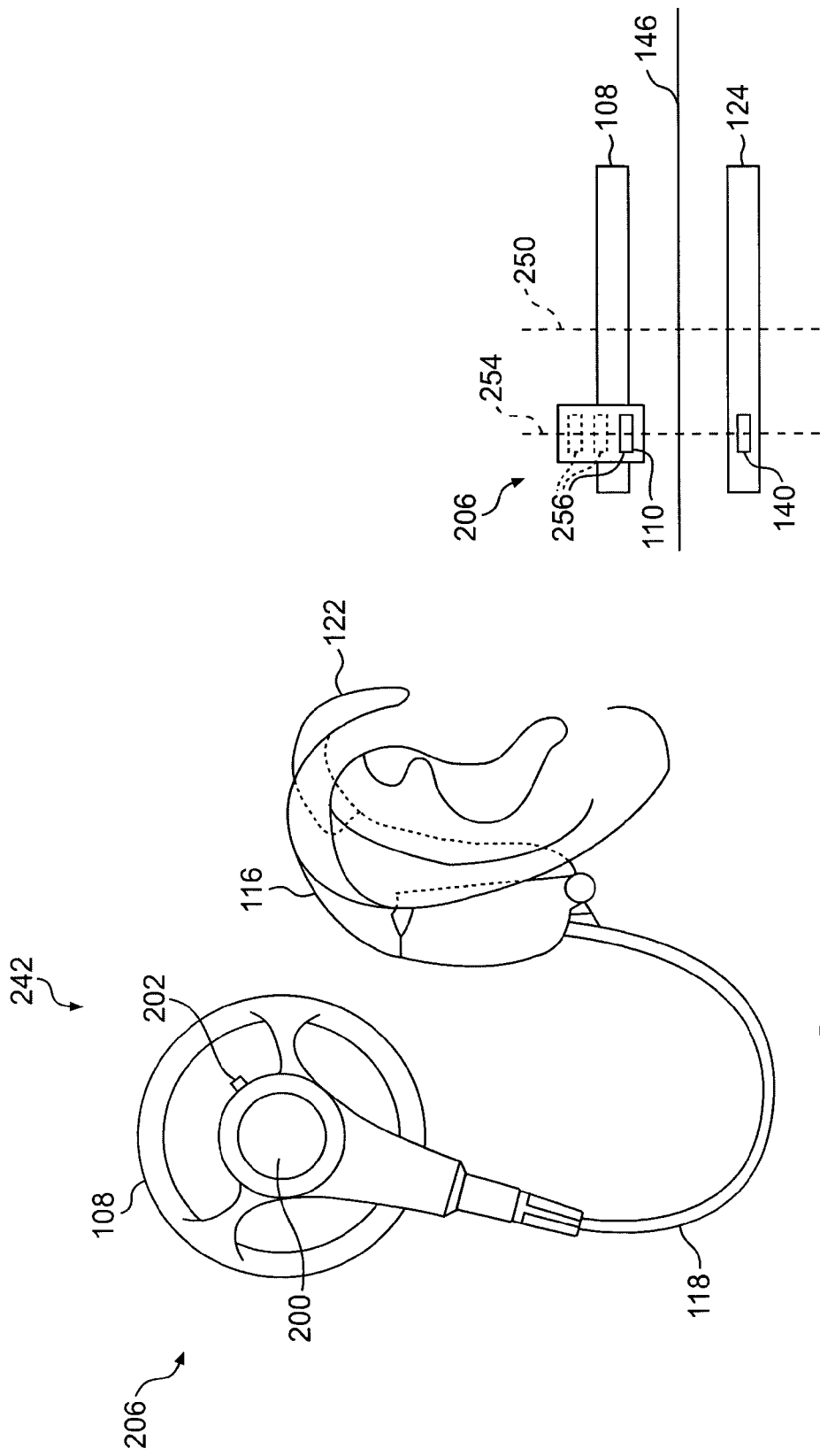

MAGNETIC ALIGNMENT APPARATUS FOR A TRANSCUTANEOUS TRANSFER SYSTEM

CROSS-REFERENCE TO RELATED APPLICATIONS

This application makes reference to the following co-pending Australian Patent No. 2003902964, entitled "Adjustment mechanism for a coil magnet," filed Jun. 13, 2003. The entire disclosure and contents of the above applications are hereby incorporated by reference.

BACKGROUND

1. Field of the Invention

The present invention relates generally to transcutaneous transfer systems and, more particularly, to a magnetic alignment apparatus for transcutaneous transfer systems.

2. Related Art

The use of implantable medical devices to provide therapy to individuals for various medical conditions has become more widespread as the advantages and benefits such devices provide become more widely appreciated and accepted throughout the population. In particular, devices such as hearing aids, implantable pacemakers, defibrillators, functional electrical stimulation devices such as cochlear prostheses, organ assist or replacement devices, and other medical devices, have been successful in performing life saving and/or lifestyle enhancement functions for a number of individuals.

Medical devices often include one or more sensors, processors, controllers or other functional electrical components that are permanently or temporarily implanted in a patient. Many such implantable devices require power and/or require communications with external systems that are part of or operate in conjunction with the medical device. One common approach to provide for the transcutaneous transfer of power and/or communications with an implantable component is via a transcutaneous transfer system.

One type of medical device that may include a transcutaneous transfer system is a cochlear implant system. Cochlear implant systems provide the benefit of hearing to individuals suffering from severe to profound hearing loss. Hearing loss in such individuals is due to the absence or destruction of the hair cells in the cochlea which transduce acoustic signals into nerve impulses. Cochlear implants essentially simulate the cochlear hair cells by directly delivering electrical stimulation to the auditory nerve fibers. This causes the brain to perceive a hearing sensation resembling the natural hearing sensation normally delivered to the auditory nerve.

Conventional cochlear implant systems primarily include external components directly or indirectly attached to the body of the patient (sometimes referred to herein as the recipient), and internal components which are implanted in the patient. The external components typically comprise a microphone for detecting sounds, a speech processor that converts the detected sounds into a coded signal, a power source, and an external transmitter antenna coil. The internal components typically comprise an internal receiver antenna coil, a stimulator located within a recess of the temporal bone of the recipient, and an electrode array positioned in the recipient's cochlear.

Collectively, the external transmitter antenna coil and the internal receiver antenna coil form an inductively-coupled coil system of a transcutaneous transfer system. The external transmitter antenna coil is usually positioned on the side of a recipient's head directly facing the implanted antenna coil to allow for the coupling of the coils to enable energy to be transferred from the external to the internal antenna coil. The transfer of energy is controlled to effect the transmission of the coded sound signal and power from the external speech processor to the implanted stimulator unit. Conventionally, the communications link has been in the form of a radio frequency (RF) link, although other such links have been proposed and implemented. Once the coded signal has been transmitted to the implanted receiver antenna coil it is provided to the implanted stimulator unit which processes the coded signal and outputs a stimulation signal to the intra-cochlear electrode assembly which applies the electrical stimulation directly to the auditory nerve of the recipient.

To facilitate the proper alignment of the external transmitter coil and the internal receiver coil, the coils sometimes include a magnet at or near the hub of the coil. The external transmitter coil is held in place and in proper alignment with the implanted antenna coil due to the attraction force of the magnets.

SUMMARY

In one embodiment of the invention, a transcutaneous transfer system is disclosed. The system comprises: an inductively-coupled coil system comprising an external and an internal coil adapted to be transcutaneously juxtaposed along a coupling axis; an internal magnet fixed relative to the internal coil; an external magnet assembly coupled to the external coil; and an apparatus to securely retain the magnet assembly in a desired one of a plurality of positions along a longitudinal axis substantially parallel to the coupling axis in response to tool-less manipulation of the apparatus.

In another embodiment of the invention, a magnetic alignment apparatus for use in a transcutaneous transfer system comprising an inductively-coupled coil system comprising an external and an internal coil adapted to be transcutaneously juxtaposed along a coupling axis; an internal magnet fixed relative to the internal coil and an external magnet assembly coupled to the external coil. The apparatus comprises: a cylindrical magnet cover configured to house the external magnet to form a magnet assembly, the cover having a differential channel disposed thereon; a differential control member comprising a sleeve adapted to slidingly receive the magnetic assembly, a user control member disposed on an exterior surface of the control member, and a differential arm extending from an interior surface of the sleeve to be disposed in the differential channel; and a housing comprising an interior volume in which the magnet assembly and differential control member are disposed, and a slide aperture through which the user control member extends, wherein tool-less manual rotation of the user control member causes an orthogonal displacement of the magnet assembly along a longitudinal axis substantially parallel to the coupling axis in response to tool-less manipulation of the apparatus.

In a further embodiment of the invention, a transcutaneous transfer system is disclosed. The system comprises: an inductively-coupled coil system comprising an external and an internal coil adapted to be transcutaneously juxtaposed along a coupling axis; an internal magnet fixed relative to the internal coil; an external magnet assembly coupled to the external coil; and an apparatus to securely retain the magnet assembly in a desired one of a plurality of positions along a longitudinal axis substantially parallel to the coupling axis in response to tool-less manipulation of the apparatus.

BRIEF DESCRIPTION OF THE DRAWINGS

FIG. 2A is a perspective view of the external component of magnetic alignment system according to one embodiment of the present invention.

FIG. 2B is a schematic block diagram showing the operation of one embodiment of the magnetic alignment apparatus of the present invention.

FIG. 5A is an exploded perspective view of the components of magnetic alignment apparatus in accordance with one embodiment of the present invention.

FIG. 5B is perspective view of the magnetic alignment apparatus of FIG. 5A shown assembled.

DETAILED DESCRIPTION

Embodiments of the present invention are described below in connection with one embodiment of an exemplary transcutaneous transfer system implemented in one type of implantable device, a cochlear prosthesis (also referred to as a cochlear implant system, cochlear prosthetic device and the like). Cochlear prostheses use direct electrical stimulation of auditory nerve cells to bypass absent or defective hair cells that normally transducer acoustic vibrations into neural activity. Such devices generally use multi-contact electrodes inserted into the scala tympani of the cochlea so that the electrodes may differentially activate auditory neurons that normally encode differential pitches of sound. Such devices are also used to treat a smaller number of patients with bilateral degeneration of the auditory nerve. For such patients, a cochlear prosthetic device provides stimulation of the cochlear nucleus in the brainstem.

Figure 1:
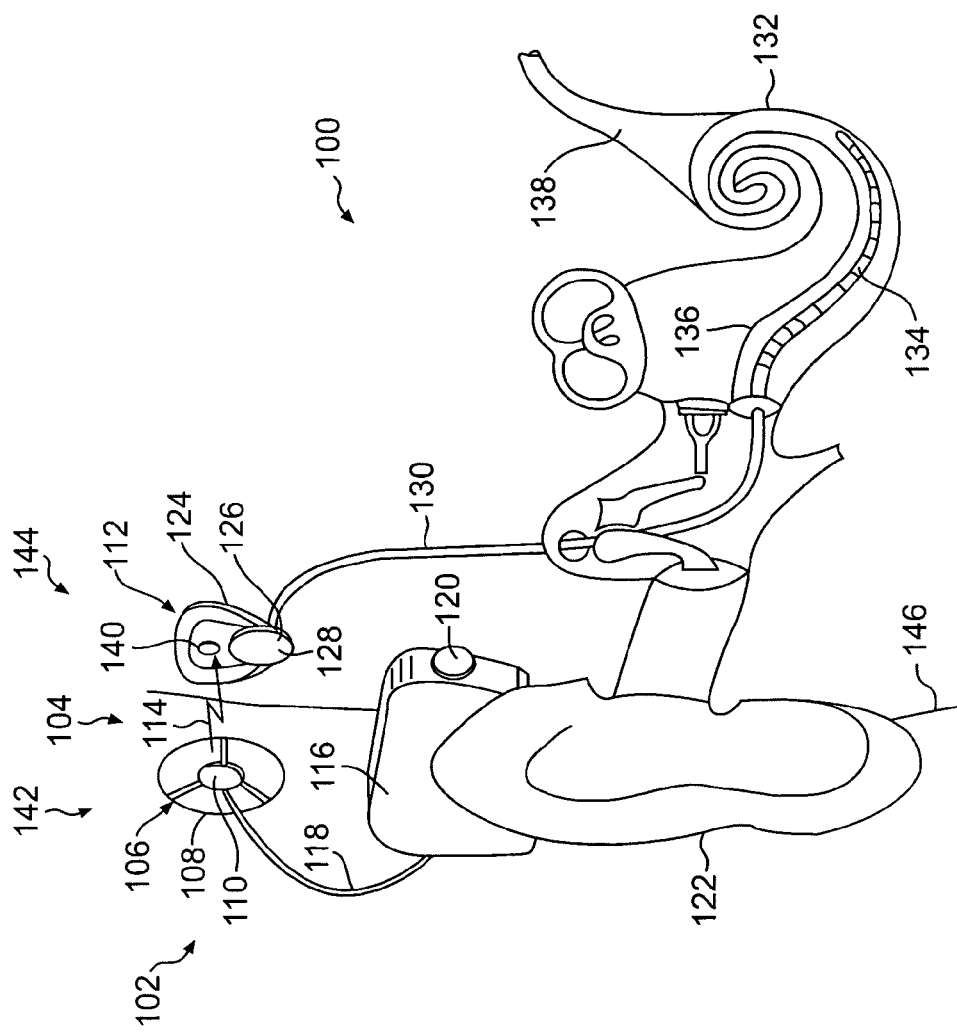
FIG. 1 is a perspective view of internal and external components of a cochlear implant system shown in their operational position on a recipient.

Exemplary cochlear prostheses in which the present invention may be implemented include, but are not limited to, those systems described in U.S. Pat. Nos. 4,532,930, 6,537,200, 6,565,503, 6,575,894 and 6,697,674, which are hereby incorporated by reference herein. FIG. 1 is a schematic diagram of an exemplary cochlear implant system 100 in which embodiments of the present invention may be implemented. Cochlear implant system 100 comprises external components 142 which are directly or indirectly attached to the body of the recipient, and internal components 144 which are temporarily or permanently implanted in the recipient. External components 142 typically comprise a microphone 120 for detecting sounds, a speech processor 116 that converts the detected sounds into a coded signal, a power source (not shown), and an external transmitter unit 106. External transmitter unit 106 comprises an external coil 108 and a magnet 110 secured directly or indirectly to external coil 108. Speech processor 116 processes the output of microphone 120 that is positioned, in the depicted embodiment, on the ear 122 of the recipient. Speech processor 116 generates a coded signal which is provided to external transmitter unit 106 via cab 118

Internal components 144 comprise an internal receiver unit 112, a stimulator unit 126, and an electrode array 134. Internal receiver unit 112 comprises an internal receiver coil 124 and a magnet 140 fixed relative to internal coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to the basilar membrane 136 thereby stimulating the auditory nerve 138.

Collectively, transmitter antenna coil 108 (or more generally, external coil 108) and receiver antenna coil 124 (or, more generally internal coil 124) form an inductively-coupled coil system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone moulding (not shown). In use, implantable receiver unit 112 can be positioned in a recess of the temporal bone adjacent ear 122 of the recipient.

Implantable receiver unit 112 has a magnet 140 embedded within the silicone housing of internal coil 124 to allow transcutaneous alignment of external coil 108 of external transmitter unit 106 and internal coil 124 of internal receiver unit 112. This magnetic transcutaneous alignment provides an attraction force that is designed to maintain external coil 108 in place on the head of the recipient without the necessity for any additional clips or other holding means. This magnetic transcutaneous alignment also facilitates the correct lateral alignment of external coil 108 over internal coil 124 to permit the efficient transmission of power and/or data.

FIG. 2A is a perspective view of one embodiment of the external components of a cochlear prosthesis, referred to herein as exterior components 242, in which one embodiment of the present invention is implemented. External components 242 comprise an exterior transmitter unit 206 implementing a magnetic alignment apparatus 200 of the present invention. Exterior transmitter unit 206 also comprises an exterior coil 108. In addition to magnetic alignment apparatus 200, external components 206 also comprise speech processor 116 connected to magnetic alignment system 200 via cable 118. The operation of magnetic alignment apparatus 200 is described next below in connection with FIG. 2B.

FIG. 2B is a schematic representation of external and internal coils 108, 124, and magnetic alignment apparatus 200. External and internal coils 102, 124 are to be laterally aligned with each other to enable the efficient transfer of energy across skin 146. In FIG. 2B, for example, both coils 108, 124 have a similar orientation relative to a coupling axis 250. The coils 108, 124 are approximately parallel with each other and are positioned closely to each other on opposing sides of skin 146. The distance between internal and external coils 108, 124 along coupling axis 250 determines the effectiveness of the coupling of the two coils; that is, the shorted the distance between external and internal coils 108, 124 the greater the coupling efficiency.

As shown in FIG. 2B, when magnets 110, 140 are aligned with each other so too are coils 108, 124. Thus, by aligning magnets 110, 140, magnetic alignment apparatus 200 enables the recipient to also align coils 108, 124. Then, once laterally aligned, external coil 108 is retained in its proper operating position relative to internal coil 124 by the strength of the magnetic attraction between internal and external magnets 110, 140, as determined by the recipient or other person manually adjusting the distance between external and internal coils 108, 124.

The strength of magnetic attraction experienced between external and internal magnets 110, 140 is determined by the position of external coil 108 along longitudinal axis 254. As noted, in the application of a cochlear prosthesis such as cochlear implant system 100 introduced above with reference to FIG. 1, internal coil 124 is stationary and cannot be adjusted other than by surgical means. Thus, magnetic alignment apparatus 200 adjusts the position of external magnet 110 relative to stationary internal magnet 140. Magnetic alignment apparatus 200, shown schematically in FIG. 2B, is a self-contained apparatus that is fixedly secured to external coil 108 and which is configured to securely position external magnet 108 at a desired one of a plurality of positions 256 along a longitudinal axis 254, which is substantially parallel to coupling axis 250 of coils 108, 124. Such desired location of external magnet 110 is achieved in response to the tool-less manipulation of a user control interface of the apparatus. As shown in FIG. 2A, user control interface is provided as a thumb-tab 202 extending from the side of magnetic alignment apparatus 200. As will be described below, thumb-tab 202 and other embodiments of the user control interface are each adjustable by a person (the recipient or another) while external coil 108 is operationally located on the recipient. Advantageously, such adjustments are made without the use of tools or other components; that is, embodiments of magnetic alignment apparatus of the present invention are self-contained and require tool-less hand operations.

While using magnets has proven an effective way to ensure coils 108 and 124 are laterally aligned, the strength of the magnetic attraction required may vary from individual to individual. For example, in some individuals having relatively thicker skin between the external and the internal coils 108, 124, there is a need for the strength of the magnetic attraction to be greater than is necessary for those individuals having relatively thinner skin 146. Should those individuals having a relatively small skin thickness employ a high strength external magnet 110 to maintain external coil 108 in place, they may experience pain or discomfort in the region of the head proximal the coil due to the pressures associated with the holding force. Conversely, should those individuals having thicker skin employ an external magnet 110 of relatively weak strength, the coils may de-couple due to the magnetic attraction forces failing to maintain external coil 110 in alignment with internal coil 140 over such a distance.

The present invention prevents such occurrences by enabling a recipient to adjust the position of external magnet 110 along longitudinal axis 254 to a position that comfortably and reliably maintains external coil 108 in operational alignment with internal coil 124. As noted, this adjustment is provided by a hand-operated control member 202 that is manipulable by the recipient without tools and during operation of the device. In addition, embodiments of magnetic alignment apparatus 200 are self-contained; that is, no components other than those provided in the apparatus itself are required to make a desired positional adjustment of external magnet 110. Also, embodiments of magnetic alignment apparatus 200 securely retain external magnet 110 in the selected position along longitudinal axis 254; that is, it is self-locking. This ensures the external magnet 110 does not change position in response to external forces.

It should be appreciated that the embodiment shown in FIG. 2B is schematic only and does not represent the relative or absolute size, dimensions, orientation or other characteristics of magnetic alignment apparatus 200 or external transmitter unit 206. It should also be appreciated that in the embodiment shown in FIG. 2B, longitudinal axis 254 is adjacent to and substantially parallel with coupling axis 250. However, in certain other embodiments, external coil 108 is provided with a centrally mounted magnet 110 that is adjustable along coupling axis 250 towards and away from the head of the recipient, in other words axis 254 and axis 250 are coexistent in such an embodiment.

Figure 3A:
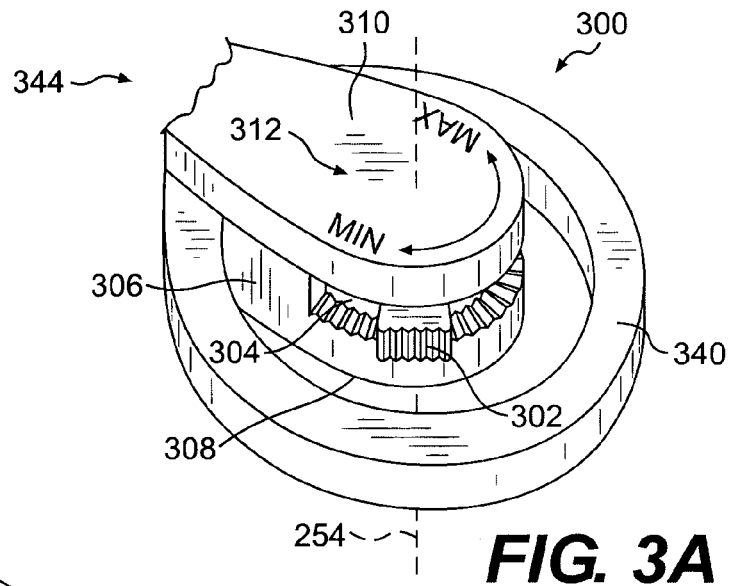
FIG. 3A is a perspective view of an assembled magnetic alignment apparatus in accordance with an alternative embodiment of the present invention.
Figure 3B:
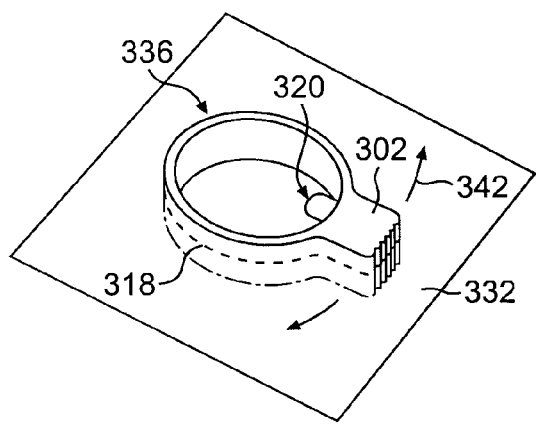
FIG. 3B is a perspective view of a differential control member used in the embodiment shown in FIG. 3A.
Figure 3D:
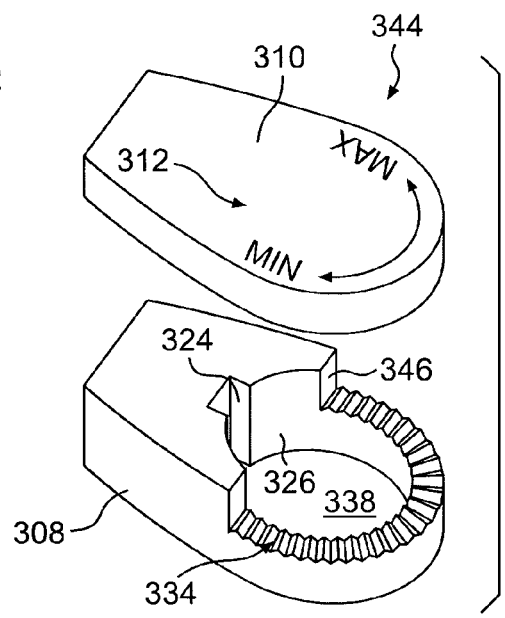
FIG. 3D is a perspective view of the displacement control housing used in the magnetic alignment apparatus shown in FIG. 3A.
Figure 3C:
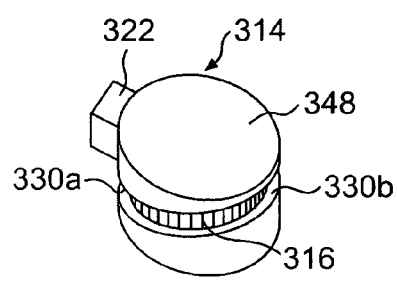
FIG. 3C is a perspective view of an external magnet assembly used but not shown in the magnetic alignment apparatus shown in FIG. 3A.

FIGS. 3A-3D are perspective views of one embodiment of the magnetic alignment apparatus 200, referred to herein as magnetic alignment apparatus 300. FIG. 3A is a perspective view of an assembled magnetic alignment apparatus 300. FIG. 3B is a perspective view of a differential control member 336 used in the embodiment shown in FIG. 3A. FIG. 3C is a perspective view of an external magnet assembly 314 used but not shown in the magnetic alignment apparatus 300 shown in FIG. 3A. FIG. 3D is a perspective view of the displacement control housing 344 shown in FIG. 3A.

Magnetic alignment apparatus 300 comprises displacement control housing 344 in which external magnet 110 is housed. As will be described in detail below, displacement control housing 344 securely retains external magnet 110 in one of a plurality of positions along longitudinal axis 254, and permits external magnet 110 to be displaced along longitudinal axis 254 only; external magnet 110 cannot be laterally displaced relative to longitudinal axis 254.

As noted, magnetic alignment apparatus of the present invention is fixedly secured in external coil 108. In the embodiment shown in FIGS. 3A-3D, magnetic alignment apparatus 300 has an integrated coil support frame 340 which preferably is centrally located in external coil 110. In one embodiment, coil control frame 340 is a separate element attached to displacement control housing 344 while in other embodiments, coil support frame 340 is integral with at least a portion of displacement control housing 344.

Referring to FIG. 3D, displacement control housing 344, in this embodiment, comprises a base 308 and a cover 310 that is secured to the housing base. As will become evident from the following description, such a two-piece construction facilitates assembly of magnetic alignment apparatus 300. Housing base 308 has a substantially cylindrical interior volume 338 suitable for restrictingly and adjustably retaining cylindrical magnet assembly 314, as described below. As one of ordinary skill in the art would appreciate, interior volume 338 may have any dimensions suitable to retain magnetic assembly 314 as described herein.

Formed in an interior wall 326 of housing base 308 is a displacement guide channel 324 which is substantially parallel with longitudinal axis 254. In the embodiment shown in FIG. 3D, step region 346 has serrations 334 formed on the surface thereof. As will be described in detail below, serrations 334 serve to facilitate the retention of magnet assembly 314 in a selected position along longitudinal axis 254. As one of ordinary skill in the art would appreciate, serrations may also be provided on the underside of housing cover 310 to be juxtaposed from serrations 334. When housing cover 310 is secured to housing base 308, cut-out or step region 346 forms an slot, referred to herein as slide aperture 304, as best shown in FIG. 3A. It should be appreciated that in alternative embodiments other approaches may be implemented to securely retain magnet assembly 314 is a desired positioning longitudinal axis 254.

Referring to FIG. 3C, external magnet assembly 314 comprises external magnet 110 and an integrated cover 348. As noted, external magnet 110, with cover 348, are retained in housing 344 which controls the displacement of the magnet assembly as it is adjusted by the recipient. In this embodiment, external magnet cover 348 has a spiral slot 316 formed therein. The spiral slot, referred to herein as differential channel 316, is defined by an upper wall 330a and a lower wall 330b. Differential channel 316 is utilized to effect a longitudinal displacement of magnet housing 314 when the recipient adjusts the hand-operated control member which, in this embodiment, is implemented as a manipulable thumb tab 302. This is described in greater detail below. Magnet cover 348 also comprises a displacement guide arm 322 extending from the surface thereof to be slidingly disposed in displacement guide channel 324 when magnet assembly 314 is disposed in interior volume 338 of housing 344.

Referring to FIG. 3B, differential control member 336 is disposed around and operationally engages magnet assembly 314 when the differential control member and the magnet assembly 314 are assembled in housing 344. Differential control member 336 comprises a sleeve 318 which, in this embodiment, is in the form of a closed ring. A differential arm 320 extends inwardly from an interior surface of sleeve 318. Differential arm 320 is dimensioned to slidingly fit into and engage differential channel 316 formed, as noted, in the surface of magnet cover 314 integral with sleeve 318 is thumb tab 302. When assembled in housing 344, sleeve 318 extends around the circumference of magnet assembly 314 below displacement guide arm 322 to enable differential arm 320 to be slidingly retained in differential channel 316. Thumb tab 302 extends through slide aperture 304 to be accessible by the recipient or other person to hand-operate to longitudinally adjust the position of magnet housing 314. This is best shown in FIG. 3A.

As noted, hand-operated control surface 302 is provided in the illustrated embodiment of magnetic alignment apparatus 300 to provide the recipient or another with the ability to manually adjust the position of external magnet 110 along longitudinal axis 254 without the use of tools or other components. Such adjustment, as noted, will cause an increase or decrease in the strength of magnetic attraction between external and internal magnets 110, 140. In the embodiment illustrated in FIGS. 3A-3D, the hand-operated control member is, as noted, implemented as a manipulable thumb tab 302. Thumb tab 302 is shown extending through slide aperture 304 formed in sidewall 306 of housing 344 in which external magnet 110 (not shown) is retained. Rotation of thumb tab 302 through the range of motion permitted by slide aperture 304 causes external magnet 110 to be displaced along longitudinal axis 254 from, for example, a position within housing 344 which is closest to internal magnet 140 to a position within housing 344 which is farthest from internal magnet 140. The range of motion of thumb tab 302 to restricted by the arc length of slide aperture 304 and length of differential channel 316. Slide aperture 302 also restricts the motion of thumb tab 302 to movement is a plane referred to herein as rotational plane 332. This restricted rotational motion is depicted in FIG. 3B by arrows 342 lying in plane 332.

External magnet cover 348 is placed inside sleeve 318 with the combined arrangement being enclosed within housing 344. Rotation of differential control member 336 through movement of extension arm 302 causes external magnet 110 to move longitudinally and at right angles to the rotation of the differential control member. There are two mechanisms that interoperate to affect the desired motion of magnet assembly 314 in response to rotation of thumb tab 302: a differential mechanism and a displacement restriction mechanism. The differential mechanism adjusts the position of magnet assembly 314 within housing 344 in response to the rotation of differential control member 336. The differential mechanism comprises the noted differential arm 320 extending inwardly from the interior surface of ring 318 to engage differential channel 316 which spiral around the surface of magnet cover 314. It should be appreciated that embodiments of the differential mechanism of the present invention may convert motion other than rotational motion in plane 332 into longitudinal displacement of magnet assembly 314. For example, in an alternative embodiment, tool-less manipulation of a user control interface that travels in a straight line in plane 332 or otherwise can cause the longitudinal displacement of magnet assembly 314. It should also be appreciated that the relationship between the motion imparted on the user control interface by the recipient (or another) and the resulting motion of the magnet assembly 314 may not be the same as in the above-described embodiment. For example, in the differential channel need not be spiral; it could have any configuration that results in continuous or intermittent displacement of external magnet 110 along longitudinal axis 254 in response to tool-less, manual manipulation of the implemented user control interface.

The displacement mechanism restricts the motion of magnet assembly 314 to displacement substantially parallel with longitudinal axis 254. This mechanism includes displacement guide channel 324 formed in interior wall 326 of housing base 308, along with displacement guide arm 322 which extends from the surface of magnet cover 348 to engage guide channel 324. When external magnet assembly 314 and sleeve member 318 are positioned within retainer housing base 308, guide arm 322 extends into channel 324 to prevent rotational movement of external magnet assembly 314 relative to housing 314. However, external magnet 110 may still be moved in a substantially longitudinal direction 254 relative to housing 344 by movement of extension arm 320 along spiral slot 316. That is, external magnet 110 is displaced in a direction which is substantially orthogonal to the rotation of differential control member 336. As one of ordinary skill in the art would appreciate, embodiments of the displacement mechanism may implement other means for restricting the motion imparted in magnet assembly 314 to longitudinal displacements.

In operation, movement of external magnet 110 is achieved by a force exerted by differential arm 302 on either upper wall 330a or lower wall 330b as differential arm 320 is manually forced along differential channel 316. Because external magnet assembly 314 is prevented from moving in the same rotational plane 332 as the differential control member 336 by the extension of displacement guide arm 322 into displacement guide channel 324 of housing 308, the force against upper 30a or lower 30b walls of channel 316 causes magnet 110 to be pushed up or down in a longitudinal direction 254 relative to retainer housing 308.

Indicia 312 is provided on the exterior surface of retainer housing 344 to provide the recipient or another with a visual indication of the change in the strength of magnetic attraction which is effected by a movement of thumb tab 302. Cover 310 has indicia 312 thereon that inform the recipient which direction to move extension arm 302 depending on whether a relative increase or decrease in magnetic attraction is desired. Indicia 312 also provides the recipient with an indication of the attachment strength of the magnet so that they can instantly assess whether there is a need to increase or decrease this strength, depending on the activity they intend on performing.

Figure 4A:
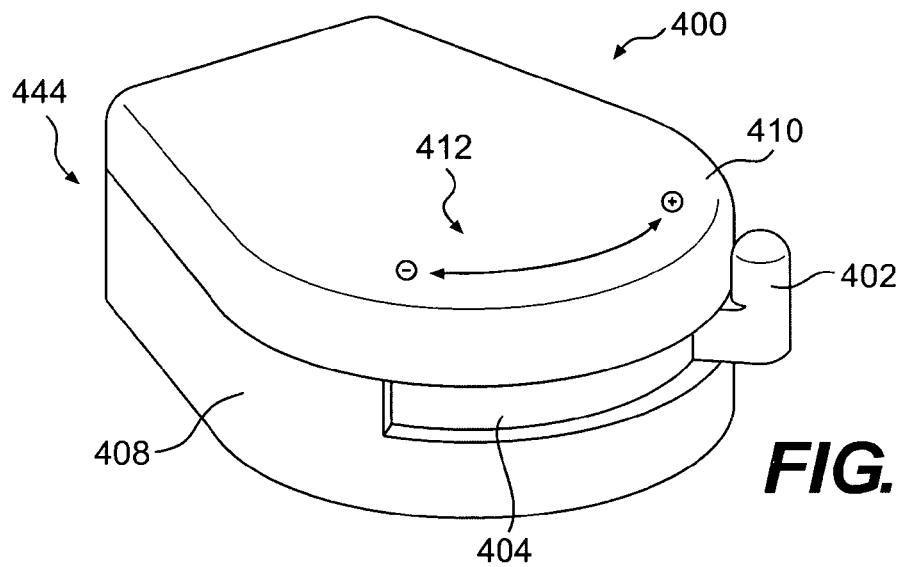
FIG. 4A is a perspective view of an assembled magnetic alignment apparatus in accordance with one embodiment of the present invention.
Figure 4B:
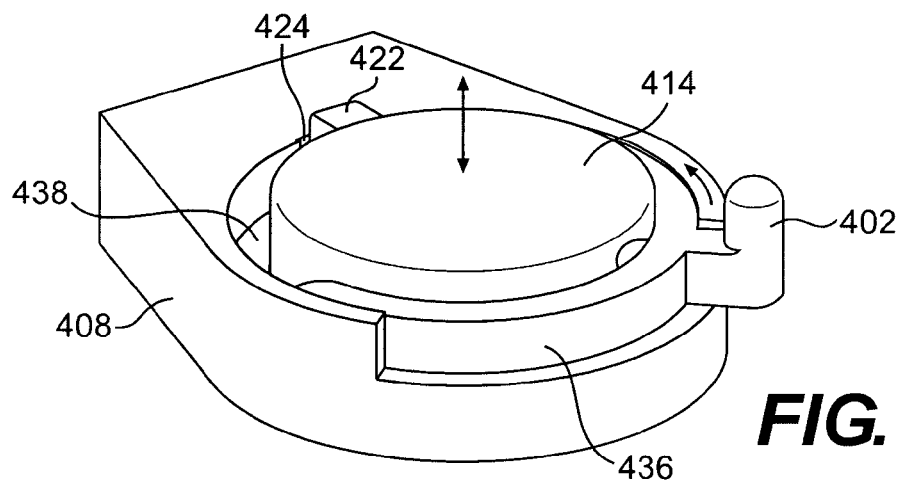
FIG. 4B is a perspective view of the magnetic alignment apparatus shown in FIG. 4A with the housing cover removed to expose external magnet assembly and differential control member disposed therein.
Figure 4C:
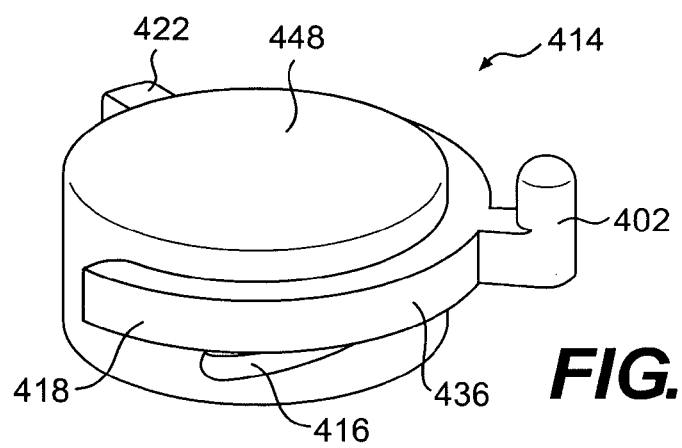
FIG. 4C is a perspective view of the external magnet assembly and differential control member shown in FIG. 4B.
Figure 4D:
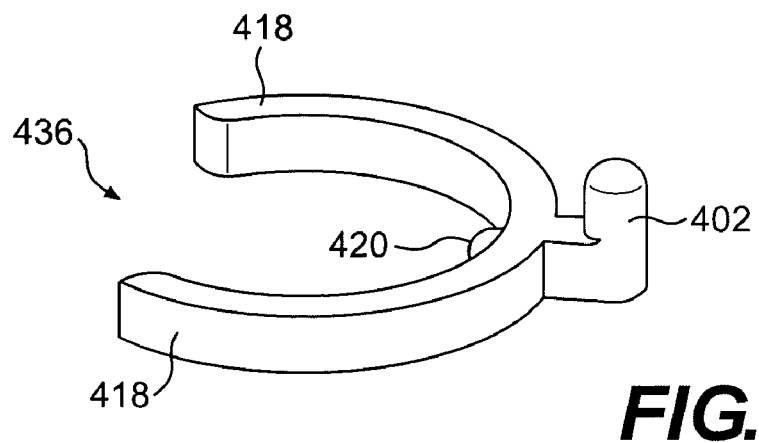
FIG. 4D is a perspective view of the differential control member shown in FIG. 4B.
Figure 4E:
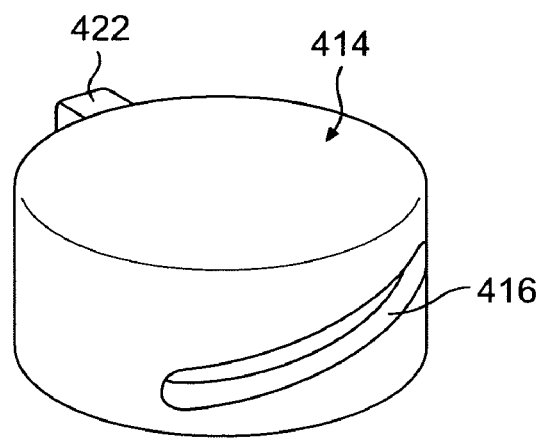
FIG. 4E is a perspective view of the external magnet assembly shown in FIG. 4B.
Figure 4F:
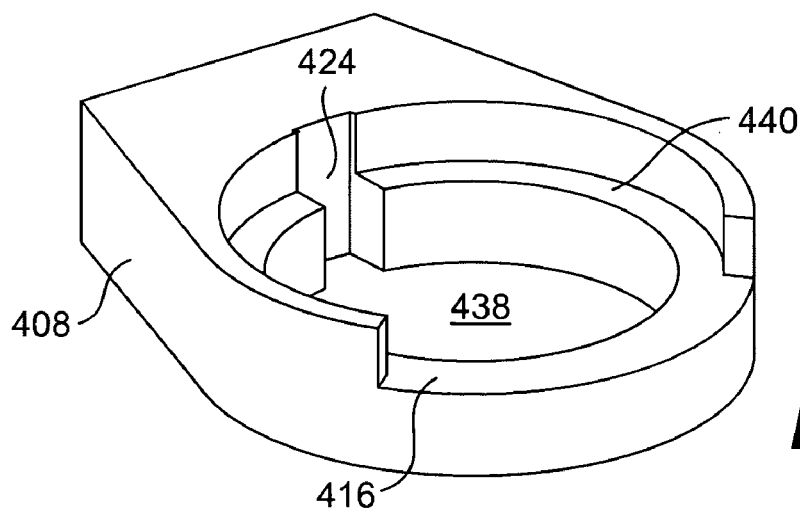
FIG. 4F is a perspective view of the base portion of the displacement control housing 444 shown in FIG. 4A.

FIGS. 4A-4F are perspective views of a magnetic alignment apparatus in accordance with an alternative embodiment of the present invention, referred to herein as magnetic alignment apparatus 400. FIG. 4A is a perspective view of an assembled magnetic alignment apparatus 400. FIG. 4B is a perspective view of the magnetic alignment apparatus 400 shown in FIG. 4A with the housing cover 410 removed to expose external magnet assembly 414 and differential control member 436 disposed therein. FIG. 4C is a perspective view of the external magnet assembly and differential control member shown in FIG. 4B. FIG. 4D is a perspective view of the differential control member shown in FIG. 4B. FIG. 4E is a perspective view of the external magnet assembly shown in FIG. 4B. FIG. 4F is a perspective view of the base portion of the displacement control housing 444 shown in FIG. 4A.

In this embodiment, the user control interface is in the form of a handle 402 that extends out through a slide aperture 404 formed in a sidewall of displacement control housing 444 in which external magnet assembly 414 is housed. Handle 402 has a portion substantially parallel with longitudinal axis 254 to facilitate grasping and control of differential control member 436. Sleeve 418 of differential control member 436 is formed by a pair of arc-shaped arms which extend around magnet assembly 414 as described below. The arc-shaped arms 418 define a substantially semi-circular spacing therebetween, into which is received cylindrical magnet assembly 414.

Displacement control housing 444 comprises base 408 and a cover 410 which has indicia 412 on the upper surface thereof proximal to slotted region 404 of sidewall 408. Indicia 412 provide an indication of the strength of the magnetic attraction force of alignment apparatus 400 with respect to the placement of handle 402. In this regard, the "+" sign indicates that when handle 402 is moved in that direction the magnetic holding and aligning force of the apparatus is the strongest, and when handle 402 is moved in the direction of the "−" sign, the force becomes progressively weaker.

Housing base 408 has a hollow central portion 438, in which external magnet assembly 414 is disposed. As noted in connection with the embodiment described above with reference to FIGS. 3A-3D, a displacement guide channel 424 is provided in the interior surface of housing base 408 to receive displacement guide arm 422 extending from magnet assembly 414. A recessed portion extends internally around the perimeter of interior volume 438 defining a seat 450, which is described in greater detail below.

Cylindrical magnet cover 448 is provided with a spiral differential channel 416 in the surface thereof. Differential channel 416 is, in this embodiment, in the form of a spiral slot that extends through cover 448. Differential arm 420 is in the form of a pin or lug that extends from the interior surface of differential control member 436 to engage differential channel 416. Differential arm 420 engages with spiral differential channel 416 of magnet assembly 414, when differential control member 436 and magnet assembly 414 are brought together.

When differential control member 436 and magnet assembly 414 are placed in the hollow central portion 438 of control housing 444, arc-shaped arms 418 rest upon seat 450 of housing base 408, and displacement guide arm 422 is received in displacement guide channel 424 provided in the rear wall of housing base 408.

In operation, horizontal movement of the tab member 402 along spiral slide aperture 404 causes differential arm 420 to travel along differential channel 416, causing magnet assembly 414 to move up or down approximately parallel to longitudinal axis 254, as shown by the arrows in FIG. 8. This vertical movement of external magnet 110 alters the strength of the magnetic force holding external coil 108 in alignment with internal coil 124, by increasing the distance between the implanted magnet 140 and external magnet 110. As the lower surface of the housing 444 is intended to directly contact the recipient's head, the strength of the magnetic alignment and holding force can be increased by moving external magnet 110 closer to the lower surface of retainer housing 444, or reduced by moving the external magnet away from the lower surface of the housing.

Figure 5A:
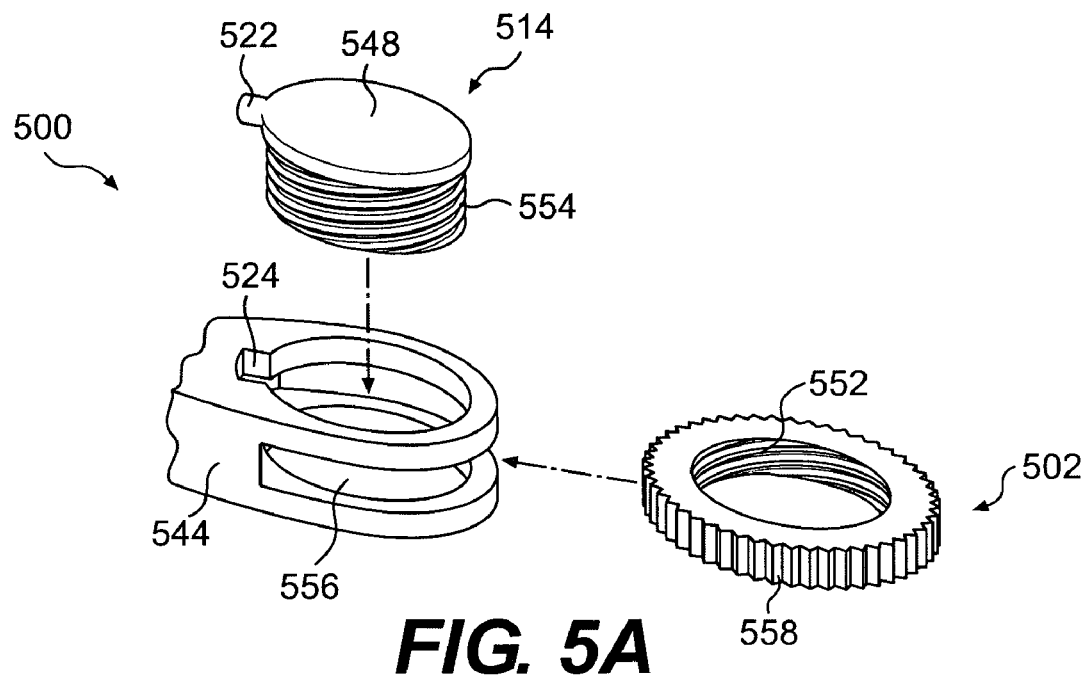
FIGS. 5A-5B are perspective views of a magnetic alignment apparatus in accordance with another embodiment of the present invention.
Figure 5B:
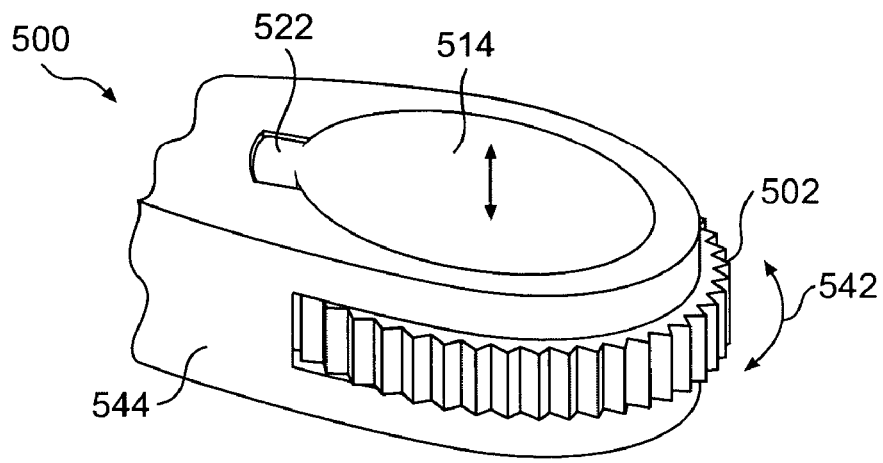

FIGS. 5A-5B are perspective views of an alternative embodiment of the magnetic alignment apparatus of the present invention, referred to herein as magnetic alignment apparatus 500. FIG. 5A is an exploded perspective view of the components of magnetic alignment apparatus 500 while FIG. 5B shows magnetic alignment apparatus 500 assembled.

In this embodiment, the user control interface is implemented as an annulus 502 having an outer surface 558 that is preferably configured to facilitate gripping by the person adjusting magnetic alignment apparatus 500. In the embodiment shown in FIGS. 5A and 5B, for example, outer surface 558 is serrated. Annulus 502 also has a threaded interior surface 552.

Displacement control housing 544 comprises an interior region dimensioned to receive magnetic assembly 514 described below. An aperture 556 is formed in housing 544 such that interior surface 552 of anulus 502 receive magnetic assembly 514.

Magnetic assembly 514 comprises external magnet 110 (not shown) housed inside magnetic cover 548. As with the above embodiments, a displacement guide arm 522 extends from the surface of magnetic cover 548 to engage a displacement guide channel formed in an interior wall of displacement control housing 544. Threads 554 are formed in the surface of magnet cover 548 to engage threads 552 of annulus 502. In this embodiment, displacement guide arm 522 is part of a top portion that is pivotally connected to the threaded portion of magnet cover 548.

When assembled, magnet assembly 514 is inserted into the recess in housing 544, and passes through annulus 502 which is received in slotted section 556 of housing 544. In this arrangement, rotation of annulus 502 in one direction causes rotation of the threaded portion of magnet housing 548 in an opposite direction and hence relative longitudinal movement of magnet assembly 514 relative to displacement control housing 544. Advantageously, the recipient (or another) can adjust the strength of magnetic attraction experienced by the coils 108, 124 without the use of tools or other components, and while external coil 108 is operationally located on the recipient.

Thus, embodiments of the magnetic alignment apparatus of the present invention maintains the external coil in alignment with the implanted coil and which can easily be adapted to suit the preferences of individual recipients without causing undue pain or inconvenience. This is particularly important when a particular recipient's lifestyle requires a transcutaneous transfer system that can operate in a variety of environments that impose a variety of forces on the external coil. For example, a recipient may require a particularly strong attraction force to be applied to the external coil when they perform physical exercise such as jogging, but require a more comfortable attraction force if they are performing non-physical activity such as reading or working. Embodiments of the present invention provide such flexibility while not requiring tools, additional components or the removal of the external coil from its operational position on the recipient.

It will be appreciated by persons skilled in the art that numerous variations and/or modifications may be made to the invention as shown in the specific embodiments without departing from the spirit or scope of the invention as broadly described. As one example, the external magnet is housed in magnet cover to form magnet assembly. It should be understood, however, that the magnet cover need not be a separate element that the external magnet. Rather, they can be monolithic and composed of the same magnetic material. As another example, the above embodiments of the magnetic alignment apparatus were presented as part of a cochlear implant system. It should be appreciated however, that the magnetic alignment apparatus could also be used in other devices now or later developed in which transcutaneous alignment of coils or other communicating components antennae is required. For example, the present invention can be implemented in a transcutaneous transfer system designed to transfer energy across a recipient's skin to power an internal device, commonly referred to as a transcutaneous energy transfer (TET) system. The present invention can also be implemented in transcutaneous transfer systems that transfer communication signals across the skin of a recipient to control, transfer data or otherwise communicate with an implanted device. As another example, it should be appreciated by those of ordinary skill in the art that the transcutaneous transfer system can be considered to include other, related components, such as signal driver circuitry located in external controller and signal processing circuitry located, in this application, in internal stimulator unit. The present embodiments are, therefore, to be considered in all respects as illustrative and not restrictive.

What is claimed is:

1. A transcutaneous transfer system comprising:
   an external and an internal coil adapted to be transcutaneously juxtaposed along a coupling axis;
   an internal magnet fixed relative to said internal coil;
   an external magnet assembly coupled to said external coil; and
   a control element, comprising a hand-operated control member, configured to allow, without movement of the external coil, manual adjustment and retention of said external magnet assembly in a desired one of a plurality of positions along a longitudinal axis substantially parallel to said coupling axis.

2. The system of claim 1, wherein said external magnet assembly comprises:
   an external magnet; and
   a magnet cover configured to at least partially house said external magnet.

3. The system of claim 2, wherein said external magnet and said magnet cover are separate integrated elements.

4. The system of claim 1, wherein said control element comprises:
   a differential mechanism configured to allow manual adjustment of said magnet assembly in response to manipulation of the hand-operated control member; and
   a displacement mechanism configured to restrict said magnet assembly displacements to those which are substantially parallel with said longitudinal axis.

5. The system of claim 4, wherein said control element further comprises:
   a differential control member comprising a sleeve adapted to slidingly receive said magnetic assembly, and the hand-operated control member, wherein the hand-operated control member is disposed on an exterior surface of said differential control member; and
   a housing, fixedly secured to said external coil and having an interior volume in which said magnet assembly and differential control member are at least partially disposed;
   and wherein said magnet assembly is cylindrical.

6. The system of claim 5, wherein said differential mechanism comprises:
   a differential channel disposed on an exterior surface of said magnet assembly; and
   a differential arm that extends inwardly from an interior surface of said differential control member sleeve to engage said differential channel, wherein said differential channel is configured such that tool-less rotation of said differential control member causes a longitudinal displacement of said magnet assembly.

7. The system of claim 6, wherein said differential channel has a spiral configuration.

8. The system of claim 6, wherein said differential channel is formed in at least a portion of an exterior surface of said magnet assembly.

9. The system of claim 6, wherein said sleeve extends at least partially around said external magnet assembly.

10. The system of claim 6, wherein said housing comprises a slide aperture through which said hand-operated control member extends so as to be accessible to a recipient, wherein the manipulation of said hand-operated control member causes said differential control member to rotate.

11. The system of claim 6, wherein said control element further comprises:
    a displacement guide channel disposed in an interior wall of said housing so as to be substantially parallel with said longitudinal axis; and
    a displacement guide arm extending from a surface of said magnet cover to engage said displacement guide channel, wherein said displacement guide arm is disposed in and travels along said displacement guide channel in response to manipulation of said differential control member, thereby restricting said magnet assembly to displacements.

12. The system of claim 1, wherein said external and internal magnets are secured to their respective coils such that when said magnets are aligned with each other so too are said respective coils.

13. The system of claim 12, wherein said internal and external magnets are centrally located relative to their respective internal and external coils.

14. The system of claim 1, wherein said control element is self-contained.

15. The system of claim 1, wherein said transcutaneous transfer system is implemented in an implantable device.

16. The system of claim 15, wherein said implantable device is a cochlear implant system.

17. A magnetic alignment apparatus for use in a transcutaneous transfer system comprising an inductively-coupled coil system comprising an external and an internal coil adapted to be transcutaneously juxtaposed along a coupling axis; an internal magnet fixed relative to the internal coil and an external magnet assembly coupled to said external coil, said apparatus comprising:
- a cylindrical magnet cover configured to at least partially house said external magnet to form a magnet assembly, said cylindrical magnet cover having a differential channel disposed thereon;
- a differential control member comprising a sleeve adapted to slidingly receive said magnetic assembly, a user control member disposed on at least a portion of an exterior surface of said control member, and a differential arm extending from an interior surface of said sleeve to be disposed in said differential channel; and
- a housing comprising an interior volume in which at least a portion of said magnet assembly and differential control member are disposed, and a slide aperture through which a hand-operated control member extends, wherein rotation of said hand-operated control member causes an orthogonal displacement of said magnet assembly along a longitudinal axis substantially parallel to a coupling axis in response to manipulation of said apparatus.

18. The system of claim 17, wherein said transcutaneous transfer system is implemented in an implantable device.

19. The system of claim 18, wherein said implantable device is a cochlear implant system.

20. A transcutaneous transfer system comprising:
- an external and an internal coil adapted to be transcutaneously juxtaposed along a coupling axis;
- an internal magnet fixed relative to said internal coil;
- a magnet assembly coupled to said external coil; and
- a control element, comprising a hand-operated control member, configured to allow manual adjustment and retention of said magnet assembly, without movement of the external coil, in a desired one of a plurality of positions along a longitudinal axis substantially parallel to said coupling axis.

21. The system of claim 20, wherein said magnetic assembly comprises:
- an external magnet; and
- a magnet cover configured to house said external magnet.

22. The system of claim 20, wherein the control element comprises:
- differential means for adjusting the position of said magnet assembly in response to the manipulation of the hand-operated control member; and
- displacement means for restricting magnet assembly displacements to those which are substantially parallel with said longitudinal axis.

23. A transcutaneous transfer system, having an internal coil coupled to an internal magnet and external coil coupled along a coupling axis to an external magnet, the external magnet disposed in a housing, comprising:
- means for receiving a manual adjusting force from an operator;
- means for translating said external magnet in said housing in a desired one of a plurality of positions along a longitudinal axis substantially parallel to said coupling axis in response to said manual adjusting force from the operator;
- means for transferring said adjusting force to said means for translating;
- means for guiding the translating of said external magnet along the longitudinal axis; and
- means for incrementally moving said external magnet within said housing.

24. The system of claim 23, wherein said means for incrementally moving said external magnet comprise screw-threading.

25. The system of claim 23, wherein said means for incrementally moving said external magnet comprise serrations.

26. The system of claim 23, wherein said transcutaneous transfer system is implemented in an implantable device.

27. The system of claim 26, wherein said implantable device is a cochlear implant system.

* * * * *